(12) United States Patent
Perrenoud et al.

(10) Patent No.: US 10,369,272 B2
(45) Date of Patent: Aug. 6, 2019

(54) MULTIPORT DELIVERY DEVICE

(71) Applicant: Enspero Inc., Carlsbad, CA (US)

(72) Inventors: Nicholas Perrenoud, Carlsbad, CA (US); Paul Swaney, Carlsbad, CA (US)

(73) Assignee: Enspero Inc., Redlands, CA (US)

( * ) Notice: Subject to any disclaimer, the term of this patent is extended or adjusted under 35 U.S.C. 154(b) by 381 days.

(21) Appl. No.: 15/156,086

(22) Filed: May 16, 2016

(65) Prior Publication Data

US 2016/0361488 A1 Dec. 15, 2016

Related U.S. Application Data (60) Provisional application No. 62/175,941, filed on Jun. 15, 2015.

(51) Int. Cl.
| | | |
|---|---|---|
| *A61M 5/14* | (2006.01) | |
| *A61M 5/165* | (2006.01) | |
| *A61M 5/38* | (2006.01) | |
| *A61M 39/10* | (2006.01) | |
| *A61M 39/24* | (2006.01) | |

(52) U.S. Cl.
CPC .......... *A61M 5/1408* (2013.01); *A61M 5/38* (2013.01); *A61M 39/105* (2013.01); *A61M 39/1055* (2013.01); *A61M 39/24* (2013.01); *A61M 2005/1406* (2013.01); *A61M 2205/75* (2013.01)

(58) Field of Classification Search
CPC .............. A61M 5/1408; A61M 5/38; A61M 2039/1072; A61M 2039/1077; A61M 2039/1083; A61M 2039/1088; A61M 2039/1094; A61M 39/1011; A61M 39/1055; A61M 39/105; A61M 2039/087; A61M 2039/1033; A61M 2205/75; A61M 2005/1406

See application file for complete search history.

(56) References Cited

U.S. PATENT DOCUMENTS

| | | | |
|---|---|---|---|
| 3,957,082 A * | 5/1976 | Fuson | A61M 5/1408 137/625.41 |
| 5,620,427 A | 4/1997 | Werschmidt et al. | |

(Continued)

FOREIGN PATENT DOCUMENTS

| | | |
|---|---|---|
| CN | 2203882 Y | 7/1995 |
| EP | 1987855 A2 | 11/2008 |

(Continued)

OTHER PUBLICATIONS

International Search Report and Written Opinion, dated Sep. 1, 2016, for International Application Serial No. PCT/US2016/032762 filed on May 16, 2016.

(Continued)

*Primary Examiner* — Jenna Zhang
(74) *Attorney, Agent, or Firm* — K&L Gates LLP; Louis C. Cullman; Georgia N. Kefallinos (57) ABSTRACT

Described herein are devices for delivering at least two different medications without requiring disconnections and reconnections of medication syringes. In some embodiments, the devices can accommodate at least two syringes simultaneously. In some embodiments, the device can be torqued while delivering the at least two different medications without loosening the outlet port from an intravenous line the device is hooked up to.

9 Claims, 7 Drawing Sheets

(56) References Cited

U.S. PATENT DOCUMENTS

| | | | |
|---|---|---|---|
| 6,508,791 B1* | 1/2003 | Guerrero | A61M 5/1408 604/183 |
| 9,764,126 B2* | 9/2017 | Tornblom | A61M 39/223 |
| 2002/0099360 A1* | 7/2002 | Bierman | A61M 39/10 604/523 |
| 2003/0040700 A1 | 2/2003 | Hickle et al. | |
| 2003/0220616 A1* | 11/2003 | Kraus | A61M 5/1411 604/252 |
| 2004/0201216 A1* | 10/2004 | Segal | A61M 39/10 285/401 |
| 2005/0267445 A1* | 12/2005 | Mendels | A61M 39/10 604/534 |
| 2006/0089604 A1* | 4/2006 | Guerrero | A61M 5/1408 604/247 |
| 2007/0093764 A1* | 4/2007 | Guerrero | A61M 5/1408 604/284 |
| 2009/0030373 A1* | 1/2009 | Gill | A61M 39/0208 604/151 |
| 2009/0137969 A1 | 5/2009 | Colantonio et al. | |
| 2012/0029465 A1 | 2/2012 | Wu et al. | |
| 2012/0234757 A1* | 9/2012 | Martin | A61M 5/165 210/650 |
| 2013/0072048 A1* | 3/2013 | Schafer | H01R 13/622 439/372 |
| 2015/0177467 A1* | 6/2015 | Gniadek | G02B 6/3894 385/58 |

FOREIGN PATENT DOCUMENTS

| | | | | |
|---|---|---|---|---|
| WO | WO 0054830 A1 * | 9/2000 | | A61M 5/1408 |
| WO | WO-0054830 A1 * | 9/2000 | | A61M 5/1408 |
| WO | 2008/045042 A1 | 4/2008 | | |

OTHER PUBLICATIONS

International Application Serial No. PCT/US2016/032762 filed on May 16, 2016.

* cited by examiner

MULTIPORT DELIVERY DEVICE

CROSS-REFERENCE TO RELATED APPLICATIONS

This application claims the benefit of U.S. provisional patent application No. 62/175,941 filed on Jun. 15, 2015, the entire disclosure of which is incorporated herein by reference.

FIELD

The present invention relates generally to multi-port, multi-formulation introduction devices.

SUMMARY

Described herein generally are multi-port, multi-formulation intravenous (IV) delivery devices that can allow a physician, advanced practice nurse, nurse, provider, or the like to deliver several time sensitive formulations such as medications while reducing and/or eliminating chances of infection, particle infusion, air infusion, or a combination thereof.

In one embodiment, devices for delivering at least two different medications are described. The devices can deliver two, three, four, five, six, seven, eight, nine, ten, or more medications. The devices can comprise a body section including at least two inlet ports. In some embodiments, at least one of the at least two inlet ports includes an anti-reflux valve and is operably connected to a first filter. In certain embodiments, one of at least two inlet ports includes an anti-reflux valve and is operably connected to a first filter and another inlet port of the at least two inlet ports includes an anti-reflux valve and is operably connected to a second filter. The devices can further include a rotating outlet port joined to the first filter and the second filter by a y-connector and configured to connect to an intravenous line. In some embodiments, the outlet port can be a fixed luer lock. In some embodiments, the devices can be torqued, spun, and/or rotated while delivering the at least two different medications without loosening the outlet port from the intravenous line.

In some embodiments, the first filter can be a 0.2 µm filter and the second filter can be a 5 µm filter. In some embodiments, at least one inlet port flows into the first filter and at least one inlet port flows into the second filter.

The at least two inlet ports described can be scrubbable inlet ports. In other embodiments, the devices can include two inlet ports. In other embodiments, the devices can include four or eight or more inlet ports.

The devices described can have a minimal amount of dead space within the devices and/or the device lines.

In some embodiments, the rotating outlet port includes a gear and a pawl that can allow rotation without loosening the outlet port from the intravenous line.

In other embodiments, the outlet port on the devices can be a male luer lock. The male luer lock can be a spinning male luer lock. In some embodiments, the male luer lock can also be a fixed luer lock that does not spin.

Methods are also descried for using the herein described devices. Methods can include methods of delivering at least two different time sensitive medications. These methods can include delivering at least a first medication in a first syringe and a second medication in a second syringe through a device into an intravenous line without disconnecting the first syringe or the second syringe.

The medications delivered using the described methods can be anesthetics. In some embodiments, an anesthetic can be propofol.

The methods can utilize a device that comprises a body section including at least two inlet ports. In some embodiments, at least one of the at least two inlet ports includes an anti-reflux valve and operably connected to a first filter and another inlet port of the least two at least one additional of the at least eight inlet ports includes an anti-reflux valve and operably connected to a second filter.

The methods can further comprise delivering at least a third medication in a third syringe through the device into the intravenous line without disconnecting the first syringe, the second syringe, or the third syringe.

Further, the methods can include delivering at least a fourth medication in a fourth syringe through the device into the intravenous line without disconnecting the first syringe, the second syringe, the third syringe, or the fourth syringe.

Further still, the methods can include delivering at least a fifth medication in a fifth syringe through the device into the intravenous line without disconnecting the first syringe, the second syringe, the third syringe, the fourth syringe, or the fifth syringe.

In one embodiment, the methods comprise delivering at least a third medication in a third syringe, a fourth medication in a fourth syringe, a fifth medication in a fifth syringe, a sixth medication in a sixth syringe, a seventh medication in a seventh syringe, and an eighth medication in an eighth syringe through the device into the intravenous line without disconnecting the first syringe, the second syringe, the third syringe, the fourth syringe, the fifth syringe, the sixth syringe, the seventh syringe, or the eighth syringe.

DETAILED DESCRIPTION

Described herein generally are intravenous (IV) infusion devices that can reduce and/or eliminate chances of infection, particle infusion, air infusion, or a combination thereof when used as directed. The devices can alleviate the need for IV port aseptic preparing and/or scrubbing between time sensitive medication deliveries.

In some embodiments, the multi-lumen devices can be anesthesia induction devices. Anesthesia delivery can be extremely time sensitive, and delivering anesthesia with the described devices can reduce the time burden on medication delivery. These devices can be scrubbable, for example, at any and all introduction ports or exit ports in the devices. Further, the devices can be self-priming meaning that air and particulates can be removed from solution(s) being delivered through the device.

Infections that patients develop while they are receiving care in a healthcare setting for another condition are termed healthcare-associated infections (HAIs). HAIs occur throughout the world, affecting hundreds of millions of patients each year. These infections are not only costly to individuals and health care systems; they can significantly increase morbidity and mortality. Seriously ill patients are particularly vulnerable to serious complications due to HAIs, likely due to factors such as progressively more invasive medical technology and complex medical procedures, increasing immunocompromised status and elderly age, and the rising incidence of antimicrobial resistance. However, many HAIs are preventable when evidence-based guidelines are incorporated into patient care.

Use of vascular catheters is common in both inpatient and outpatient care. In the United States, it is estimated that almost 300 million catheters are used each year; nearly 3 million of these are central venous catheters (CVCs), also known as central lines. Central venous catheters play an integral role in modern health care, allowing for the administration of intravenous fluids, blood products, medications, and parenteral nutrition, as well as providing hemodialysis access and hemodynamic monitoring. However, their use is associated with a risk of bloodstream infection caused by microorganisms colonizing the external and/or internal surface of the device or the fluid pathway when the device is inserted or in the course of its use. Central venous catheters are the most frequent cause of healthcare-associated bloodstream infections, called central line-associated bloodstream infections (CLABSI).

An estimated 330,000 CLABSIs occur each year in the United Satetes, 80,000 of those occur in the intensive care unit (ICU). CLABSIs are serious but often preventable infections when evidence-based guidelines are followed for the insertion and maintenance of central lines.

As with other HAIs, CLABSIs also increase the cost of health care and prolonged hospital stays by up to three weeks. Non-inflation-adjusted costs associated with CLABSIs have varied from $3,700 per infection to $36,441 per infection. A recent CDC estimate set the cost of each CLABSI at $16,550.

For many years most harm that occurred in health care was considered inevitable; fortunately, that way of thinking has been replaced in the developed world by one that categorizes harm as largely preventable. The progress that has been made in recent years in reducing CLABSIs points to their preventability, as illustrated by the following examples:

Umscheid et al. estimated that as many as 65% to 70% of CLABSIs may be preventable with the implementation of evidence-based strategies (*Infection Control Hospital Epidemiology*, 2011; 32(2): 101-114).

Pronovost and colleagues from the Johns Hopkins Quality and Safety Research Group demonstrated, initially in 103 ICUs in Michigan, that increased use of evidence-based interventions and an improved culture of patient safety can prevent CLABSIs. At the end of the 36-month study period, there was a 60% overall reduction in the baseline CLABSI rate. As a result, $200 million and an estimated 2,000 lives were saved.

Overall, the high morbidity and mortality associated with CLABSI, improved understanding of its pathogenesis and preventability, and the growing unwillingness of patients, payers, and patient advocates to look at HAIs as an acceptable risk has led to the emergence of a "zero tolerance" mind-set—an emphasis that organizations set the goal at eliminating HAIs rather than being comfortable with meeting national or local averages. Employing relatively simple evidence-based practices to reduce, if not eliminate, CLABSIs appears to be within the reach of even resource-limited settings. Within this framework, HAIs—and CLABSIs in particular—are more and more being viewed as "preventable" events.

As such, there is a need in the art for intravenous (IV) infusion devices that can reduce and/or eliminate chances of infection. Devices that can reduce and/or eliminate infection are disclosed herein.

Rapid sequence induction, also described as rapid sequence intubation (RSI), is an advanced airway management medical procedure used to achieve tracheal intubation under the induction of anesthesia in patients who are at high risk of pulmonary aspiration. Rapid sequence intubation refers to the pharmacologically induced sedation and neuromuscular paralysis prior to intubation of the trachea. The technique is a quicker form of the process normally used to induce general anesthesia.

Rapid sequence induction involves pre-filling the patient's lungs with a high concentration of oxygen gas, followed by administering rapid-onset hypnotic and neuromuscular-blocking drugs that induce prompt unconsciousness and paralysis, allowing tracheal intubation with minimal delay. Unlike other methods of induction, no artificial ventilation is provided from the time that drugs are administered until after intubation has been achieved; this minimizes insufflation of air into the stomach, which might otherwise lead to regurgitation. But also requires rapid airway management and intervention as the patient is apneic and will begin to develop oxygen-hemoglobin desaturation.

Rapid sequence induction is used where general anesthesia must be induced before the patient has had time to fast long enough to empty the stomach; where the patient has a medical condition that makes aspiration more likely during induction of anesthesia, regardless of how long they have fasted (such as gastro-esophageal reflux disease); or where the patient has become unable to control their own airway even before anesthesia (such as with the critically ill or after a traumatic brain injury).

Typically RSI is initiated in an Emergency Room, Operating Room and/or the Intensive Care Unit. It is also utilized outside of these typical hospital settings and can occur in the Emergency Medical Response settings within the scope of the practice of paramedics, firefighters, and other healthcare professionals.

The induction drugs preferentially used in RSI have short durations of action, wearing off after only minutes. This confers a degree of fault tolerance on the procedure when it is used in elective or semi-elective settings: if intubation is unsuccessful, and if the clinical condition allows it, the procedure may be abandoned and the patient should regain the ability to protect their own airway sooner than would be the case under routine methods of induction. Conversely, in emergency settings where the patient's condition does not allow for them to be woken up immediately, a failed RSI places them at very high risk for respiratory compromise.

Commonly used medications during a rapid sequence intubation include, but are not limited to, sedatives such as midazolam, ketamine, fentanyl, propofol, and etomidate, paralytics such as succinylcholine, rocuronium, vecuronium, and other medications such as atropine for patients where bradycardia is a concern, and ephedrine where hypotension may occur secondary to the sedating drugs.

Pretreatment for RSI consists of the medications given to specific groups of high-risk patients minutes before the paralysis stage with the aim of protecting the patient from the adverse effects of introducing the laryngoscope and endotracheal tube. Intubation causes increased sympathetic activity, an increase in intracranial pressure and bronchospasm. Patients with reactive airway disease, increased intracranial pressure, or cardiovascular disease may benefit from pretreatment.

Two common medications used in the pretreatment of RSI include, but are not limited to, lidocaine and atropine.

Lidocaine has the ability to suppress the cough reflex which in turn may mitigate increased intracranial pressure. For this reason lidocaine is commonly used as a pretreatment for trauma patients who are suspected of already having an increase in intracranial pressure. The typical IV dose is given three minutes prior to intubation. Lidocaine is also theorized to blunt a rise in intracranial pressure during laryngoscopy, although this remains controversial and its use varies greatly.

Atropine, as a parasympathetic blocker, may also be used as a premedication agent in pediatrics to prevent bradycardia caused by hypoxia, laryngoscopy, and succinylcholine. Atropine may be used to prevent a reflex bradycardia from vagal stimulation during laryngoscopy, especially in young children and infants. Despite their common use, such adjunctive medications have not been demonstrated to improve outcomes.

With standard intravenous induction of general anesthesia, the patient typically receives an opioid, and then a hypnotic medication. Generally the patient will be manually ventilated for a short period of time before a neuromuscular blocking agent is administered and the patient is intubated.

During rapid sequence induction, the person still receives an IV opioid. However, the difference lies in the fact that the induction drug and neuromuscular blocking agent are administered in rapid succession with no time allowed for manual ventilation.

Commonly used hypnotics include thiopental, propofol and etomidate. Commonly used neuromuscular blocking agents used include succinylcholine and rocuronium. The neuromuscular blocking agents paralyze all of the skeletal muscles, most notably and importantly in the oropharynx, larynx, and diaphragm.

Opioids such as Fentanyl may be given to attenuate the responses to the intubation process (accelerated heart rate and increased intracranial pressure). This is supposed to have advantages in patients with ischemic heart disease and those with brain injury (e.g. after traumatic brain injury or stroke).

One important difference between RSI and routine tracheal intubation is that the practitioner does not typically manually assist the ventilation of the lungs after the onset of general anesthesia and cessation of breathing, until the trachea has been intubated and the cuff has been inflated.

Human Factor Engineering (HFE) is a critical stage in medical device development. The FDA has provided guidance regarding HFE as a standard during the regulatory process. Product design plays an important role in usability, and clinical effectiveness ensuring safety while reducing human error. Estimates suggest that the FDA receives an average of 100,000 medical device incident reports per year. More than a third of those incident reports are due to user error. Furthermore, it is estimated that more than 44% of product recalls are due to design errors. A set of product design specifications (PDS) have been developed which include HFE and aim to improve the devices in the art by reducing risk of device use error, outlining proper device use, reducing need for training or user manual reference, providing safe connections to and between other products, improving user experience, detailing proper user handling, meeting ergonomic standards.

Human factor engineering is being implemented by the devices described herein through product enhancement to the following attributes: design, such as but not limited to, an ergonomic mold for handheld use and versatile compatibility, specific IV tubing ID/OD improving clinical effectiveness, specific IV tubing length adjusted for syringe accessibility, and luer collar distance from device body addressing ease of handling, materials such as but not limited to, clear PVC for fluid flow visualization, medical grade PVC for sterile applications, specified filter housing dimensions improving clinical effectiveness, specified filter membrane addressing removal of specific foreign bodies, and add on products such as, but not limited to, color coded IV tubing for fluid identification, color coded IV connectors for fluid identification, and molding, assembly and packaging by a single manufacturer.

In some embodiments, in addition to the devices being self-priming, they can also produce low waste volume. In other words, the devices can function with minimal dead volume thus providing more accurate delivery of solution(s) through the devices.

The devices described herein can also filter solution(s) that are introduced through the devices. In some embodiments, the devices have one filter. In other embodiments, the devices have more than one filter.

By providing one or more of the above features of scrubability, self-priming, filtering, and minimal dead volume delivery, the presently described devices can prevent health care workers' inadvertent IV infusion of air, microorganisms, endotoxins, particulate matter, and/or lipid emboli into a patient.

In some embodiments, the devices described herein can be used to deliver solution(s), such as formulations or medications to a patient. The patient can be a mammal such as a human, cat, dog, horse, cow, bull, goat, bison, or the like. When used with/for patients, the devices can meet the highest safety standards imposed by local, regional, or governmental regulations for introduction and maintenance of formulation delivery.

Further, because the devices can include at least two inlet ports, the devices can eliminate a need for multiple connections during introduction of formulations into a patient. Therefore, the devices can reduce overall time and the potential for contamination of the formulations during delivery. In other words, the devices can provide safe, efficient and reliable methods to perform multi-formulation delivery. In one embodiment, the devices described can assist in preventing healthcare-associated infections (HAI) which have become a growing problem in therapeutic and hospital settings.

Currently, no device exists that addresses all potential risks associated with administering IV formulations and/or medications to patients. In particular, no device exists that addresses all potential risks associated with administering IV anesthesia to patients. With the delivery of anesthesia, time is a critical factor in the delivery of different anesthetic medications and/or medications subsequent to an anesthetic medication to ensure the patient's survival.

The devices and systems described herein can include the following benefits: be sterile when opened for use, be preassembled for on demand delivery of medications, be self-priming, be closed to ambient air flow, each port/hub/cap connector can possess an ability to be aseptically prepared and/or scrubbed and/or sterilized prior to connection for access of IV medications, can filter air, can filter particulate matter, can filter lipids, can filter microorganisms and endotoxins, can limit connection to only one access of the patient's IV tubing, can include one-way/anti-reflux valves to prevent retrograde IV fluid or blood flow, can include the ability to securely isolate chosen medications dedicated to one patient, can be easy to use during a single provider rapid sequence induction of medication, and/or can include minimal dead space within the fluid pathways.

The devices described herein can include various combinations of cap/cap connectors, female lure locks, anti-reflux valves, micro-tubing, multi-lumen manifold, low volume filters, Y-connector, macro-tubing, and easy to use male lure lock(s). The systems can be customizable prior to manufacturing and individually distributed to healthcare providers as a one-time use device.

Further, the devices can improve patient safety and/or streamline the process of administering IV medications, such as anesthesia, through the reduction in errors of contaminations and infections of the patient's blood stream by eliminating inadvertent infusions of particulates and securely isolating IV medications for the use by one patient. In one embodiment, the devices can employ the highest level of infection prevention standards set by the CDC (Centers for Disease Control and Prevention), TJC (The Joint Commission), SHEA (The Society for Healthcare Epidemiology of America), World Health Organization (WHO), National Institute of Health (NIH), United States Department of Health and Human Services (HHS), European Centre for Disease Prevention and Control, Centers for Medicare, and/or Medicaid Services.

The devices can also reduce time associated with medication introduction by eliminating multiple connections and disconnections of medication syringes during the standard rapid introduction sequence.

For example, the CDC in 2011 provided the Guidelines for the Prevention of Intravascular Catheter-Related Infections. These guidelines have been developed for persons responsible for surveillance and control of infections in hospital and states at page 54: "[m]inimize contamination risk by scrubbing the access port with an appropriate antiseptic (chlorhexidine, povidone iodine, an iodophor, or 70% alcohol) and accessing the port only with sterile devices."

Likewise, the TJC recommends that a medical provider "scrub the hub you are accessing every time you use it" (CLABSI (central line associated blood stream infections) Toolkit: Valve Disinfection Guidance, Mar. 21, 2014). Scrubbing a hub every single time it is being accessed is a near impossible task when time sensitive medications, such as anesthesia, are being delivered.

Further still, SHEA has provided a 2014 Compendium which is a concise distillation of current guidelines for the prevention of HAIs that brings together recommendations from respected sources in a format suited to implementation in the clinical setting. It also includes metrics and indicators of success for implementation. The Compendium states that "[i]f CLABSI surveillance or other risk assessments suggest that there are ongoing opportunities for improvement, hospitals should then consider adopting some or all of the prevention approaches listed as special approaches". In some embodiments, the devices described herein can be categorized as a special approach under the 2014 Compendium.

Port scrubbing is a CDC recommendation, the TJC states mandatory port scrubbing prior to administration of IV medications, and SHEA considers "special approaches" for additional prevention of blood stream infections. The present devices can meet all these needs and more.

Port Scrubbing is generally considered to require at least 15 seconds of scrubbing an access port with an appropriate antiseptic prior to the administration of every IV medication. Appropriate anesthetics can be, but are not limited to, chlohexadine, providone iodine, an iodophor, or 70% alcohol.

The devices described herein can prevent and/or reduce the chance of a blood stream infection (BSI) and/or HAIs. Blood stream infections and/or HAIs can many times be associated with the contamination of IV ports and IV junctional connections during IV medication and IV fluid administration. Blood stream infections and/or HAIs are a great risk for patients that require IV medication therapy. Over 500,000 catheter-related BSIs occur in the United States every year, costing the United States healthcare system over $10 billion annually.

A patient's blood stream is a dynamic and sterile environment that, once contaminated, can pose multiple life threatening problems. Contaminations of a patient's blood stream can occur via both endogenous (e.g., patient's skin flora) and extrinsic (e.g., health care workers' hands) exposure to the medication fluid pathways. The most vulnerable populations are the immune compromised patients who include, but are not limited to, neonates, elderly, critically ill, hematology patients, oncology patients, transplant patients, and the like. Also vulnerable are those patients with an indwelling or implanted medical device including, but not limited to, central venous catheters (CVC), prosthetic joint, shunts, hardware, and the like.

Blood stream infections carry a high percentage of mortality for the vulnerable populations. It has been reported that BSIs have a reported mortality up to 25%. Blood Stream Infections can lead to endocarditis, osteomyelitis, sepsis, stroke, infected heart valves, infected joints, infected implanted devices and other life threatening illnesses. The presently described devices can reduce a patient's risk of infection by, in part, preventing connections and disconnections without proper or recommended port scrubbing.

Every IV medication administration can also potentially allow embolic air and particles into the patient's blood stream. This occurs via the fluid pathway by way of IV injection ports. The present devices can eliminate or substantially reduce embolic air introduction into an IV line.

Lipid based medication also poses a risk of inadvertent infusion of large globule molecules, which can lodge in the pulmonary vasculature compromising respiratory function. The present devices can eliminate or substantially reduce globule introduction into an IV line.

In the area of delivery of anesthesia through an IV, healthcare providers currently prepare and utilize multiple sterile, single use syringes and individually connect and disconnect them to and from the patients' IV tubing access ports. Occasionally, a healthcare provider will attach multiple syringes to a small manifold or several injection ports on a patient's IV tubing prior to the induction of anesthesia. However, the sequence of administering multiple medications during the induction of anesthesia limits the provider's ability to properly clean between medication administrations and limits the providers ability to keep the access ports, syringe tips and medications sterile for future medication administration, especially during and after the sequence of the induction of anesthesia. These risks occur in both the adult and pediatric populations in all settings in anesthesia.

The current techniques risk inadvertent infusion of particulate matter, air and lipid emboli, microorganisms and endotoxins that can be introduced to the patient's bloodstream via the inadvertent contamination of the IV medication, medication syringe, cap connector or access point connection. The probability of contamination dramatically increases with each IV access connection performed by a healthcare provider. The average induction and maintenance of anesthesia requires a range of 2-10 different IV medications, each requiring repeated connections and reconnections of separate syringes to and from the patient's IV tubing in a rapid sequence prior to initiation of airway management.

The devices described herein can provide the highest-grade standards for all IV infusions. The devices described herein can also provide the safest and/or most efficient approach to the administration of IV anesthesia, especially during the induction sequence of multiple medications of which timed delivery is critical and 15 second scrub times for each port may not be possible without compromising the patient's safety.

Medications can be loaded into separate syringes for delivery to a patient using the present devices without constant connections and disconnections. Medications that can be delivered using the presently described devices include, but are not limited to, anesthesia, antibiotics, saline, muscle relaxing agents, neuromusclar blocking agents, anxiolytics/amnesics, narcotics, stimulants, anti-nausea medications, chemotherapeutics, antimicrobials, steroids, non-steroidal anti-inflammatories, nerve blocks, vitamins, gene therapies, nutrients, emergency medications such as heart rate and blood pressure support medications, and the like.

In one embodiment, the medications can be anesthetics and the medications that support delivery of anesthesia. Anesthesia can include propofol and/or lidocaine. Antibiotics can include cefazolin which may require a saline flush. Saline can also be used to flush the device lines described herein. In one embodiment, a saline flush may be recommend to ensure the medications are delivered to the patient and are not retained within the device. Neuromuscular blocking agents can include rocuronium. Anxiolytics/amnesics can include midazolam. Narcotics can include fentanyl. Emergency medications can include phenylephrine, ephedrine, epinephrine and vasopressin. Anti-nausea medications can include ondansetron and dexamethasone.

The enumerated medications are presented as non-limiting medications. Each anesthetic poses its unique challenges, and therefore the selection of medications represents the needs or potential needs of the patient and the type of surgery's anesthesia requirements. Some anesthesia cases require less than the categories/medications listed and some require more. In some embodiments, the combinations of medications required for anesthesia for a patient can be as few as two and as many as ten or more to complete an anesthetic.

Further, the delivery of the anesthesia can be extremely time sensitive. The devices described herein can assist and/or solve problems that exist with time sensitive delivery of the medications for anesthesia. For example if eight different medications are being delivered in an anesthetic treatment, including 15 second port scrub times between medications, two minutes would be spent simply cleaning the port between each medication delivery which does not account for the actual time for delivery. For example, if propofol is the first medication delivered, there is simply not sufficient time to scrub delivery ports and deliver subsequent medications without putting a patient at risk. Thus, often ports are not aseptically prepared and/or scrubbed and contaminations and patient infections can occur. Further, because infection is being introduced directly into the bloodstream, time to sufficiently disinfect inlet ports is absolutely critical. The present devices solve these and other problems. The device, in combination with positive pressure, continuous flow infusion pump, is intended to deliver fixed doses of medication upon demand by the patient or healthcare provider.

Figure 1:
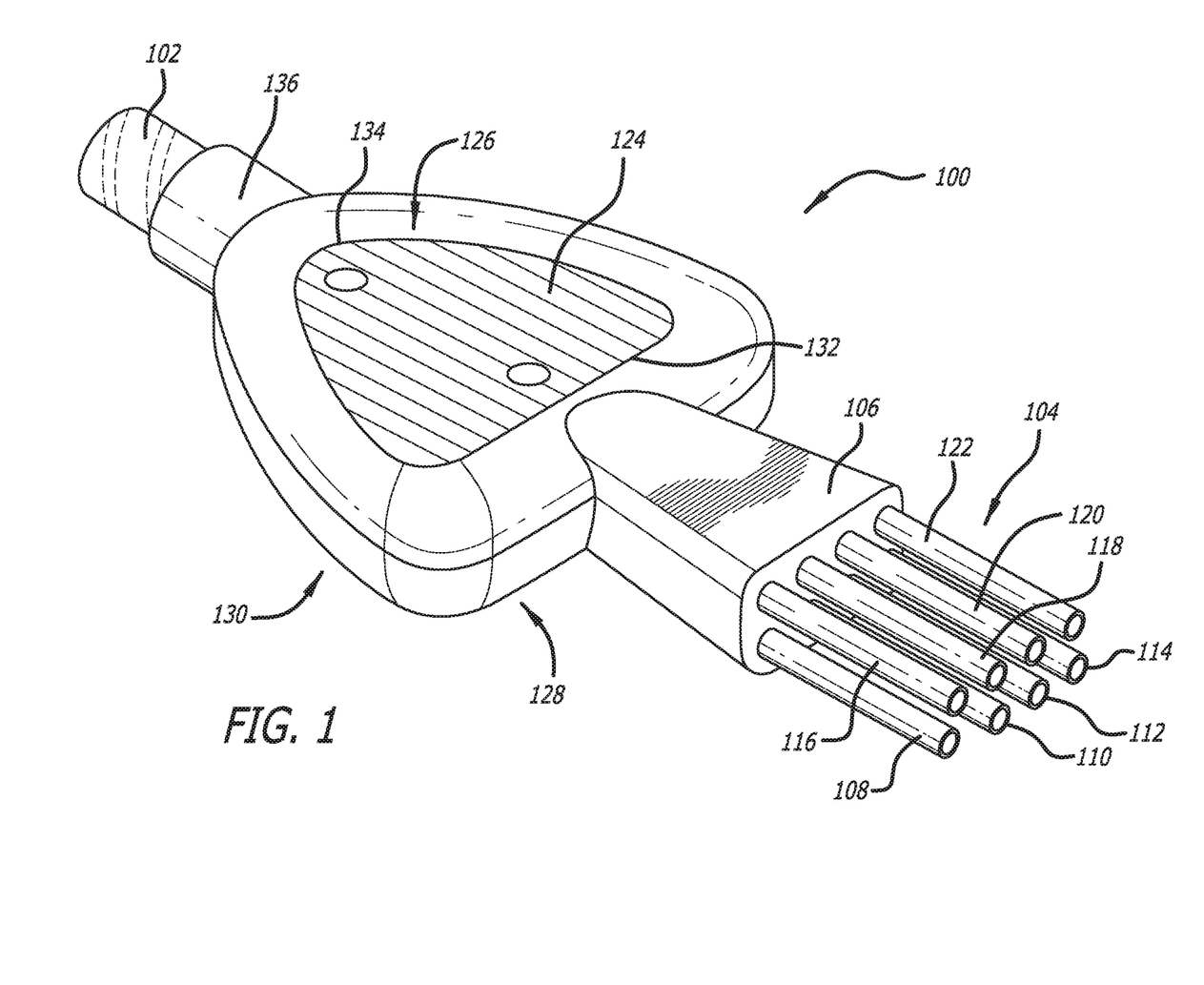
FIG. 1 illustrates an example embodiment of a device as described herein.

An example device, device 100, is illustrated in FIG. 1. Device 100 can include an outlet 102. Outlet 102 can be configured to be connected to an IV line or other introduction line. Outlet 102 can be of a standard line connector or can include anti-torqueing or spinning connectors as will be described in greater detail herein. In other embodiments, outlet can be a standard, fixed luer connection. In one embodiment, device 100 is for single patient use.

Device 100 can include at least two or more inlet lines 104 that interface or otherwise meet at hub 106. Each of the at least two or more inlet lines 104 can be the same or different size line. In one embodiment herein, device 100 includes a first inlet line 108, a second inlet line 110, a third inlet line 112, a fourth inlet line 114, a fifth inlet line 116, a sixth inlet line 118, a seventh inlet line 120, and an eighth inlet line 122. More than eight inlet lines can be included in device 100. For example, nine, ten, eleven, twelve, 13, 14, 15, or more inlet lines can be provided.

Device 100 can also include a first filter 124 on the device's first side 126 and a second filter 128 on device's second side 130. Although illustrated with only first filter 124 and second filter 128, device 100 can include any number of filters that may be required. For example, device 100 can include three, four, five, six, seven, eight, nine, ten, eleven, twelve, 13, 14, 15, or more filters. In one embodiment, device 100 can include a separate/different filter for each input associated with device 100.

Hub 106 can be located before or after one or more filters described herein. In other embodiments, hub 106 can be placed before some filters and a second hub can be placed after the filters. Any number of hubs and filters can be used in any number of combinations.

Hub 106, which can also be referred to as a manifold, can include two or more inlet lines and two or more outlet lines that enter a filter(s). In one embodiment, a hub 106 can be illustrated as in FIG. 2A and FIG. 2B. Hub 106 includes a front side 202 and a back side 204. Here, hub 106 includes a wedge shape that has a larger surface area on front side 202 when compared to back side 204. However, hub 106 can have other shapes such as a sphere, a cube, a cone, an ellipse, a spade, or the like.

In some embodiments, the internal channels of the hub can be built into a filter. For example, in some embodiments, different inlet lines can merge at a filter. In such an embodiment, the filter can help merge the inlet lines. In still other embodiments, the filters can be built into the hub. The lines running through the hub can include filters such that when the medications exit the hub, they have been filtered.

Figure 2A:
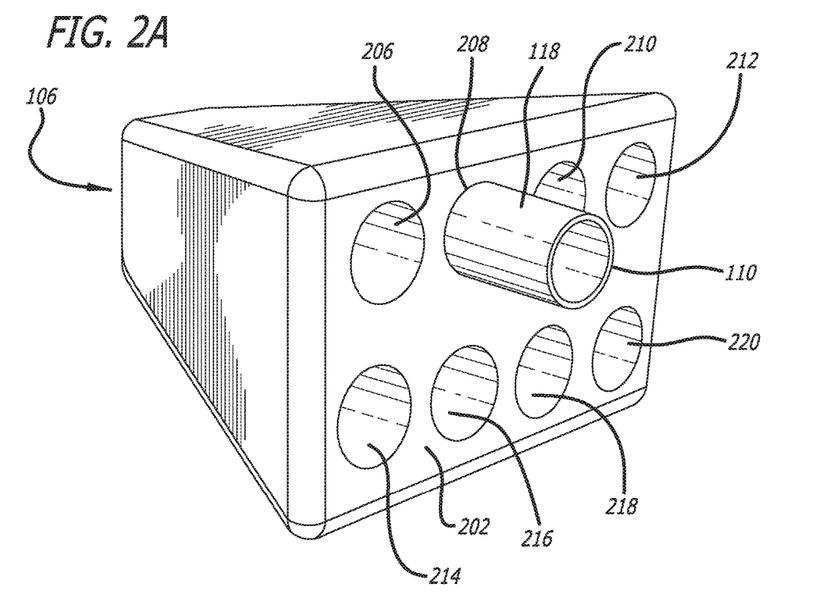
FIG. 2A is a front perspective view of a hub as described herein.

Front side 202 can include at least two or more inlet lines. In one embodiment, front side 202 includes a first inlet 206 which is fed by first inlet line 108, a second inlet 208 which is fed by second inlet line 110, a third inlet 210 which is fed by third inlet line 112, a fourth inlet 212 which is fed by fourth inlet line 114, a fifth inlet 214 which is fed by fifth inlet line 116, a sixth inlet 216 which is fed by sixth inlet line 118, a seventh inlet 218 which is fed by seventh inlet line 120, and an eighth inlet 220 which is fed by eighth inlet line 122.

Figure 2B:
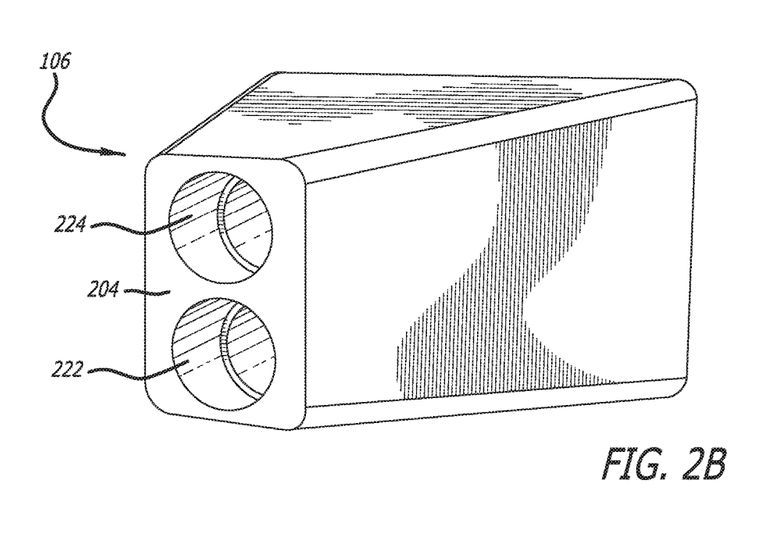
FIG. 2B is a back perspective view of a hub as described herein.

In this embodiment, back side 204 includes a first outlet 222 and a second outlet 224. However, other embodiments can include more outlets such as three, four, five, six, seven, eight, nine, ten, eleven, twelve, 13, 14, 15, or more outlets. In still other embodiments, hub 106 may only include one outlet.

With two outlets on back side 204, different combinations of the eight inlets in this embodiment can be formulated during production. In one embodiment, as illustrated in FIGS. 3A-3D, hub 106 can include first inlet 206, second inlet 208, third inlet 210, fourth inlet 212, fifth inlet 214, sixth inlet 216, seventh inlet 218, and eighth inlet 220. Here, fourth inlet 212 and eighth inlet 220 are combined within hub 106 and fed to a first filter through first outlet 222. Likewise, first inlet 206, second inlet 208, third inlet 210, fifth inlet 214, sixth inlet 216, and seventh inlet 218 are combined within hub 106 and fed to a second filter through second outlet 224. Any combination of inlet and outlet numbers can be used to deliver medications through hub 106.

In one embodiment, fourth inlet 212 and eighth inlet 220 are fed to first filter 124 and the remaining inlets can be fed into second filter 128. In another embodiment, fourth inlet 212 and eighth inlet 220 are fed to a first filter and the remaining inlets can be fed into a second filter.

Figure 3A:
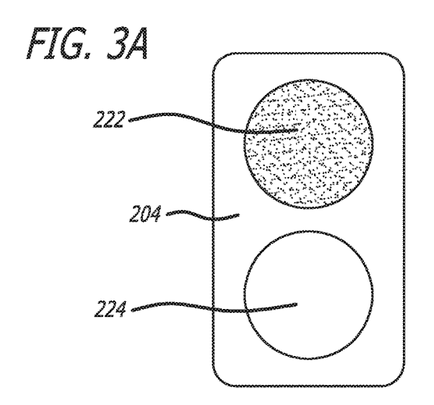
FIG. 3A is a back view of a hub as described herein.
Figure 3B:
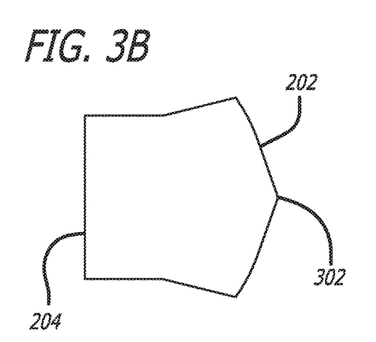
FIG. 3B is a side view of an exemplary hub.
Figure 3C:
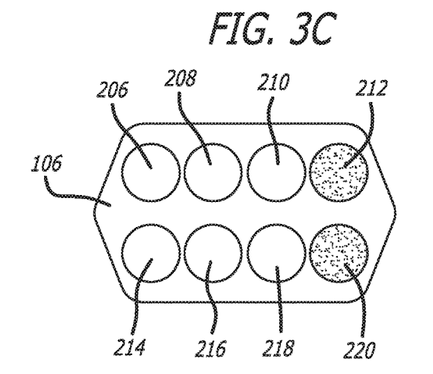
FIG. 3C is a front view of the hub in FIG. 3B.
Figure 3D:
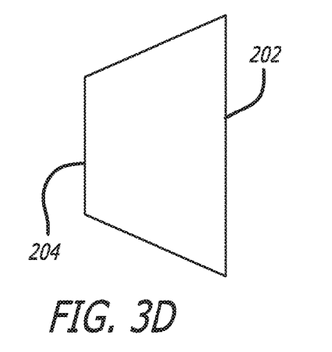
FIG. 3D is a side view of another exemplary hub.
Figure 3E:
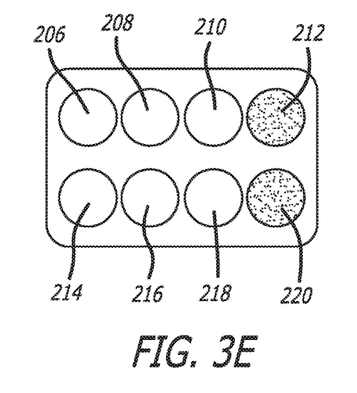
FIG. 3E is a front view of the hub in FIG. 3D.

Hub 106 can have different shapes depending on aesthetic and/or user needs. For example, front side 202 can be curved, arched, pinched, spade-like, or triangular. Example configurations are illustrated in FIGS. 3A-E. In one embodiment, as illustrated in FIG. 3B, front side 202 can be triangular with an apex point 302. Having an apex point can allow for better placement of inlet ports when many inlets ports are in close proximity. In another embodiment, as illustrated in FIG. 3D, front side 202 can simply be a flat surface.

Filters used herein can also have any number of shapes. In one embodiment, the shape of a filter can aid in the flow of a particular fluid through the filter. As illustrated in FIG. 1, filters can have a substantially triangular shape. The filter can include channels and/or flow paths that run in the direction of flow. There, first side 132 can have a larger area than second side 134 to direct flow from hub 106 to outlet 102 in an efficient manner and/or to allow for a larger area on first side 132 to allow more filtering to occur when medications first reach the filter.

In other embodiments, filters can have other shapes such as square or substantially square, rectangular or substantially rectangular, circle or substantially circular, elliptical or substantially elliptical, trapezoidal or substantially trapezoidal, spade or substantially spade, or the like.

Filters can also have different sized pores. Larger pore sizes can be used to filter substances such as lipid globules and other larger materials. Smaller pore sizes can be used to filter bacteria and/or microbes. A filter can have a 0.1 µm, 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm, 1.5 µm, 2 µm, 2.5 µm, 3 µm, 3.5 µm, 4 µm, 4.5 µm, 5 µm, 5.5 µm, 6, µm, or larger pore size. In one embodiment, first filter 124 is a 0.2 µm filter and second filter 128 is a 5 µm filter.

In other embodiments, the filters can provide much larger pore sizes for different liquid substances such as, but not limited to blood or colloid products. For example, pore sizes can be 50 µm, 100 µm, 150 µm, 200 µm, 250 µm, 300 µm, 350 µm, 400 µm, 450 µm, 500 µm, or larger, or between 50 µm and 300 µm, or between 100 µm and 500 µm.

In some embodiments, filters described herein can filter both particles and air. Filtering particles can prevent infusion of particulate matter than can disrupt blood flow into the vasculature of a patient. Filtering air in addition to particles can prevent infusion of air bubbles into the vasculature of a patient. Filtering air and/or particles can be particular importance for neonates and patient's with congenital heart disease.

The filters described herein can be set up in series or can be set up in different channels that converge at or near outlet 102. Further, at least two or more inlet lines 104 that converge at hub 106 can be fed to different filters depending on location of the inlet line, the inner diameter of the inlet line, or the like.

Any number of filters used in the described devices can feed into outlet 102. The exit of filters described herein can feed into outlet 102 through a y-connector or junction 136. Junction 136 can allow multiple filter exit lines to converge into outlet 102 with minimal dead space volume.

Outlet 102 can be any connection type that can interface with a patient's IV tubing. In one embodiment, outlet 102 can be a male luer lock. In another embodiment, outlet 102 can rotate freely around the axis of the IV tubing without loosening the connection. In other words, device 100 can freely rotate around the axis of the IV tubing without loosening the luer lock connection. In some embodiments, this luer lock can be called a spinning luer lock.

A spinning luer lock or spinning luer connector can prevent the unintentional disconnection of the device from IV tubing as a result of internal pressure unwinding. An example spinning luer lock connector 400 is illustrated in FIGS. 4A-4F. Luer connector 400 includes a collar 402 that has a cup like shape that surrounds delivery protrusion 404. Collar 402 can include internal threads 406 that can accept a female luer fitting that would exist on an IV inlet port.

Figure 4A:
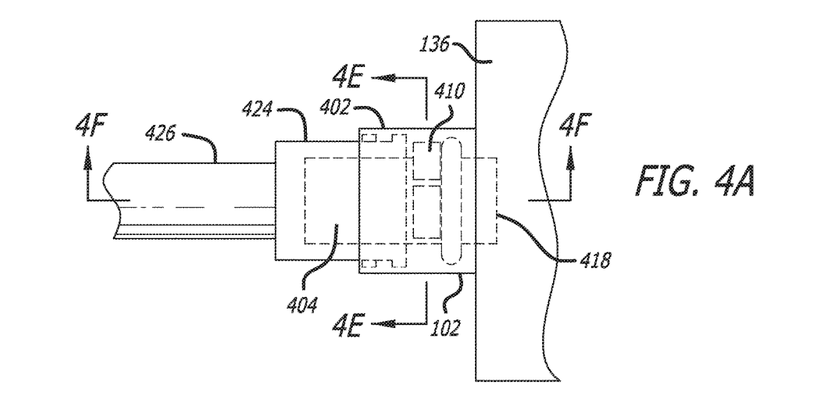
FIG. 4A illustrates an assembly of a spinning connection as described herein.
Figures 4B, 4C, 4D:
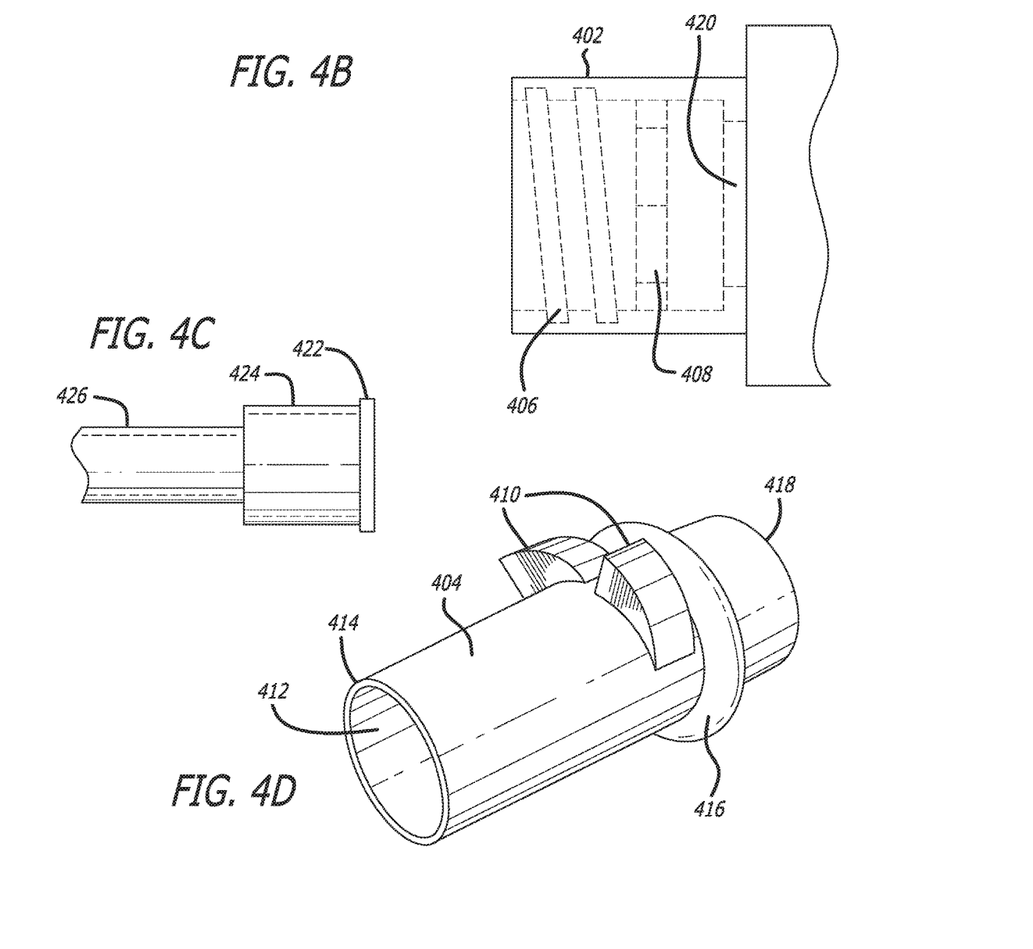
FIG. 4B illustrates the male connection of FIG. 4A.
FIG. 4C illustrates the female connection of FIG. 4A.
FIG. 4D illustrates a component of the assembly in FIG. 4A.
Figure 4E:
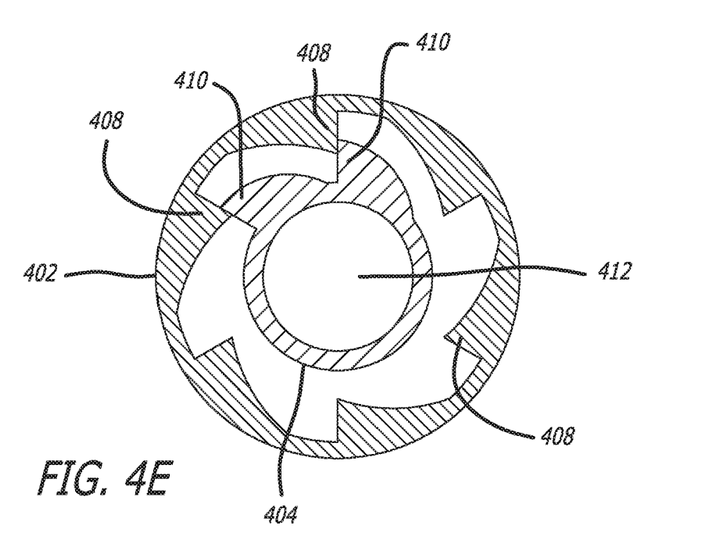
FIG. 4E is a cross-section as indicated in FIG. 4A.
Figure 4F:
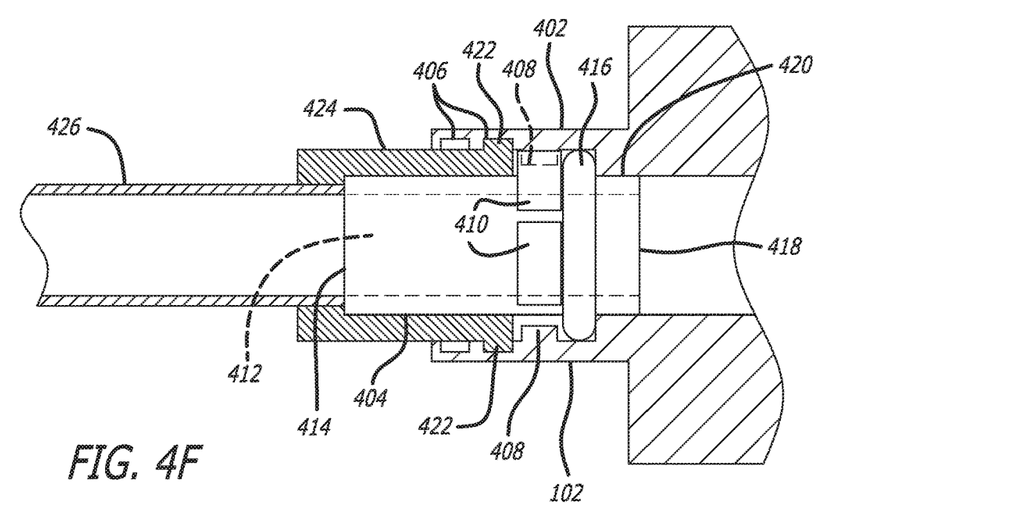
FIG. 4F is another cross-section as indicated in FIG. 4A.

In some embodiments, collar 402 can include within it a portion of a ratcheting mechanism including a gear 408 that runs around the internal circumference of collar 402. Gear 408 can lock within it a pawl 410 associated with delivery protrusion 404. An example pawl is illustrated in FIG. 4D where delivery protrusion 404 is illustrated without a collar. Here delivery protrusion 404 includes an open delivery outlet 412 at proximal end 414 and an O-ring or rib portion 416 that prevents a collar from progressing down delivery protrusion 404 from distal end 418 and seals the connection. Distal end 418 can be a continuous tube or be connected to device 100 directly.

As a device 100 is attached to a female luer connection 424 on an IV line 426, screw portion 422 is twisted into internal threads 406 until luer connection 424 is tight and secure. Even when the luer connection is tight and secure, pawl 410 engages gear 408 thereby preventing disengagement of the luer lock without physically holding collar 402 to allow disengagement of the luer lock. However, without intentionally disengaging the luer lock, device 100 can spin freely around the axis of the IV line without coming loose.

Figure 5:
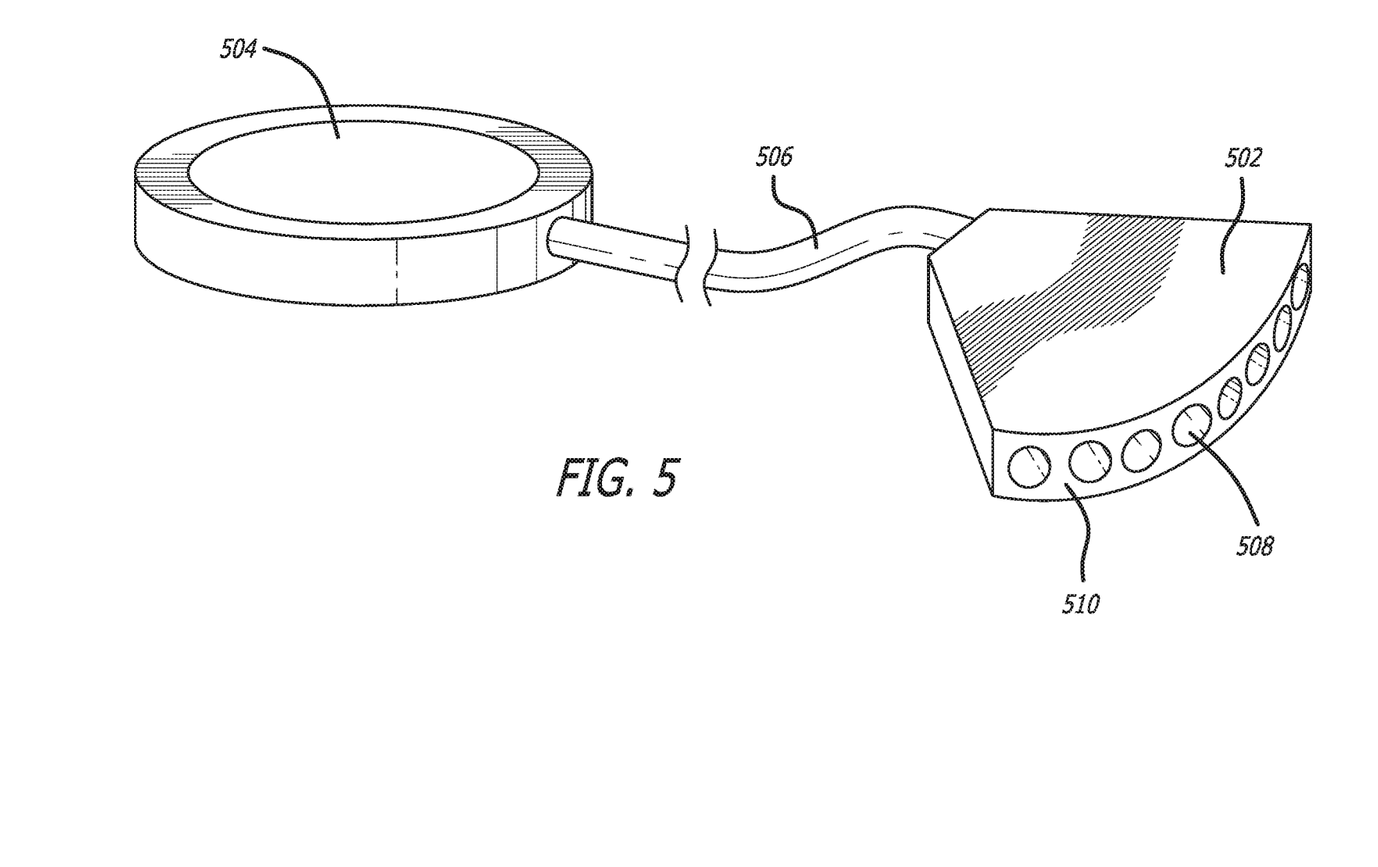
FIG. 5 illustrates an embodiment where a hub is distant to the body of the device.

In some embodiments, the hub can be situated within the body of the device itself or can be operably attached to the device's body. As illustrated in FIG. 5, hub 502 is attached to device body 504 by one or more lines 506. Such a manifold or hub can be referred to as external. In some embodiments, a device may have two, three, four, five, six, or more external hubs connected by a line. Line 506 can be permanently attached to both hub 502 and device body 504 or can be detachable from one or both of hub 502 or device body 504.

In some embodiments, multiple external hubs can assist a user in spacing of syringes. In other words, if eight different medications are to be delivered and eight closely situated syringes are difficult to navigate, they can be split between external manifolds to free up maneuvering space.

The devices herein including body portions, encasements, hubs/manifolds, and the like can be formed of rigid polymers. Exemplary polymers include, but are not limited to polyurethanes, silicones, polyesters such as polyolefins, polyisobutylene and ethylene-alphaolefin copolymers; acrylic polymers and copolymers, ethylene-co-vinylacetate, polybutylmethacrylate, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; carboxymethyl cellulose; synthetic and natural rubbers such as polysiloxanes, latex, polymerized isoprene, bromo isobutylene isoprene, chloro isobutylene isoprene, polychloroprene, chlorosulphonated polyethylene, ethylene propylene, ethylene propylene diene monomer, fluoro silicone, hydrogenated nitrile butadiene, polyisoprene, isobutylene isoprene butyl, methyl vinyl silicone, acrylonitrile butadiene, acrylonitrile butadiene carboxy monomer, styrene butadiene, epichlorodydrin; and combinations thereof. The polymer or combination of polymers chosen to form portions of the devices must be rigid enough to hold a particular configuration and perform its intended function. In some embodiments, the polymer used is a thermal set rigid plastic.

Further, as illustrated in FIG. 5, hub 502 can include one or more inlets 508 along a horizontal line. Inlets can be situated in a horizontal line in order to provide space to attach the multiple syringes needed for a particular patient.

In some embodiments, inlets described herein can be a location where a tubing line enters a hub or manifold or can be attachment points for the syringes themselves. If the inlets on a hub or manifold are syringe attachment points, they can be spaced apart sufficient to allow adjacent syringes to be attached to the hub or manifold without obstruction. For example, hub 502 in some embodiments could have a curved hub surface 510 to allow more spacing between adjacent inlets.

In some embodiments, each inlet line includes a connector for syringes, for example a needleless syringe connector. Needleless syringes can be used to prevent unintentional needle sticks and convenience for connecting and disconnecting the syringe from the presently described devices. Common luer connectors are not conducive to disinfecting prior to use. Although many luer connectors are sterile from the manufacturer, once opened in a medically relevant area, contamination can occur during device preparation and/or use. The needleless connectors used herein can have a surface that is conducive to scrubbing with disinfectant prior to use.

Any needless syringe connector can be used, for example, compression fittings, luer lock connectors, BD Q-SYTE® Luer Access Split Septum (Becton, Dickinson and Company, Franklin Lakes, N.J.), INTERLINK® Needleless IV Access Devices (Becton, Dickinson and Company, Franklin Lakes, N.J.), CARESITE® Luer Access Device (B. Braun Medical, Inc., Bethlehem, Pa.), INVISION-PLUS® IV Connector with or without Neutral Advantage Technology Rymed Technologies, LLC, Franklin Tenn.), SAFELINE® Split Septum Needleless Connector (B. Braun Medical, Inc., Bethlehem, Pa.), ULTRASITE® Ag Antibacterial Luer Access Device (LAD) (B. Braun Medical, Inc., Bethlehem, Pa.), piggyback connectors, MAXPLUS® needless connector (Medegen, Ontario, Calif.), or the like. In some embodiments, combinations of the technologies used in the above connections can be used.

Further, the inlet lines described herein can each include an anti-reflux valve to prevent back flow of medicament into the syringe once it has been delivered to the inlet line. Any anti-reflux valve can be used. In some embodiments, anti-reflux valves can be included within the needleless syringe connector. In other embodiments, the anti-reflux valves can be independent to the connectors.

In some embodiments, the outlet lines described herein can include an anti-reflux valve to prevent back flow of medicament into the device once it has been delivered to the patient's IV line. Any anti-reflux valve can be used. In some embodiments, anti-reflux valves can be included within the connector used to attach the device to the patient's IV line. In other embodiments, the anti-reflux valves can be independent to the connector.

Inlet port tubing described herein can be tubing with a minimal internal volume such as having the smallest internal diameter. In some embodiments, tubing can be microtubing. Although the tubing can have the smallest internal diameter needed, different internal diameter tubing can be used as appropriate for a particular medication being delivered through an inlet. For example, a more viscous material may require tubing with a larger internal diameter than an aqueous based medication.

Much like the tubing described herein, channels though hubs, y-connectors, and the like can have the smallest internal diameter required for delivery of medications.

Tubing and channels described can have internal diameters of less than about 0.05 mm, less than about 0.1 mm, less than about 0.2 mm, less than about 0.3 mm, less than about 0.4 mm, less than about 0.5 mm, less than about 0.6 mm, less than about 0.7 mm, less than about 0.8 mm, less than about 0.9 mm, less than about 1 mm, between about 0.05 mm and about 0.5 mm, or between about 0.05 mm and about 0.1 mm.

If tubing is used for inlets, the length of the tubing can be minimized to reduce dead volume. Inlet tubing lengths can be less than about 15 cm, less than about 14 cm, less than about 13 cm, less than about 12 cm, less than about 11 cm, less than about 10 cm, less than about 9 cm, less than about 8 cm, less than about 7 cm, less than about 6 cm, less than about 5 cm, less than about 4 cm, less than about 3 cm, or less than about 2 cm.

Although microtubing can be used, in some embodiments, macrotubing can also be used. Larger tubing may be desired if multiple medications are being pushed through the filters or if macrotubing is required for a more viscous medication. Thus, if microtubing is used for some inlets and macrotubing is used for other inlets, the device may include macrotubing at a device outlet in order to accommodate the more viscous medications.

In one embodiment, inlet ports/connectors can be configured for single use. For example, an inlet connector can include single direction locking configurations or connections that lock and break into that configuration preventing further use of the connection after its initial use. This single use inlet connection prevents subsequent use of a device as described herein. Further, this single use inlet connection prevents cross-contamination of medications in delivery syringes that may subsequently be connected to an inlet that was not single use.

In one embodiment, inlets, inlet lines, and/or inlet ports can be color coded. Color coding can assist a user in identifying a particular feature of the device and reduce error in device usage.

In some embodiments, color coding can be used to identify a particular inlet's affiliation with a filter(s). As devices herein can have multiple different filters with different inlets feeding different filter types/sizes, different inlets, inlet lines, and/or inlet ports can be color coded to represent to a user which inlets feed which filter.

In other embodiments, color coding can be used to match particular medications with particular inlets. For example, color coding can be used to identify a particular order of medication delivery. In some embodiments, syringes can be color coded to match particular inlet colors. Such color matching can ensure that medications are delivered throughout a predetermined inlet using the visual color cue.

In still further embodiments, inlets can include particular syringe locking mechanisms that match syringe locking mechanisms in order to prevent miss-attachment of a medication to an inappropriate inlet. For example, inlets feeding a larger pore size filter can include one type luer connection and inlets feeding a smaller pore size filter can include a different luer connection, wherein the two luer connections are not interchangeable. Such locking mechanism usage can ensure that medications are delivered throughout a predetermined filter by preventing attachment of a medication to an inappropriate filter.

Figure 6:
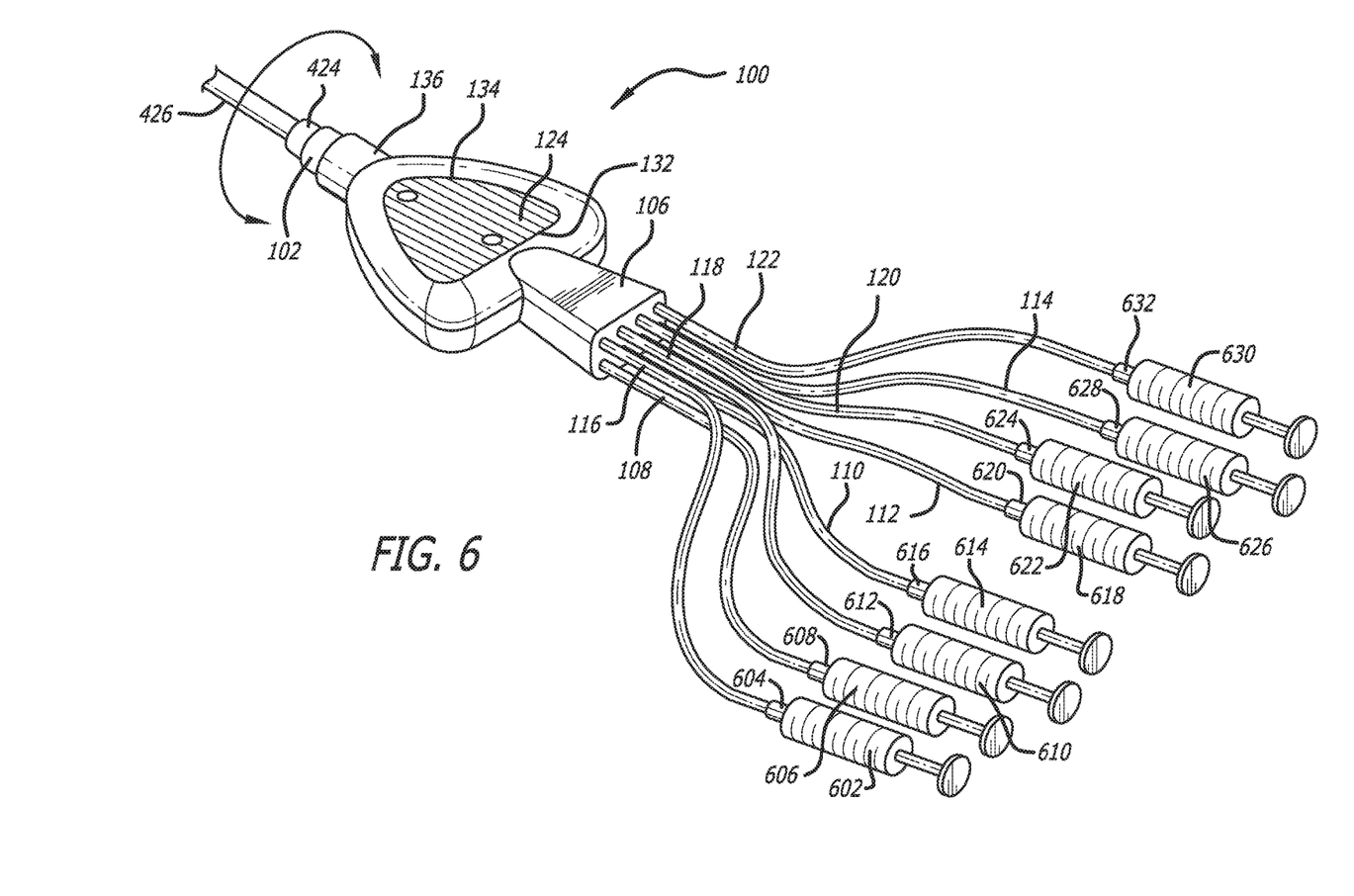
FIG. 6 is an illustration of a device assembled with eight syringes.

In one embodiment, device 100 as illustrated in FIG. 6 is assembled with syringes attached. Device 100 includes a body portion that includes filters as described herein. Hub 106 includes first inlet line 108 with a first syringe 606 attached to first connector 608, second inlet line 110 with a second syringe 614 attached to second connector 616, third inlet line 112 with a third syringe 618 attached to third connector 620, fourth inlet line 114 with a fourth syringe 626 attached to fourth connector 628, fifth inlet line 116 with a fifth syringe 602 attached to fifth connector 604, sixth inlet line 118 with a sixth syringe 610 attached to fifth connector 612, seventh inlet line 120 with a seventh syringe 622 attached to seventh connector 624, and eighth inlet line 122 with an eighth syringe 630 attached to eighth connector 632. Because syringes can be attached simultaneously, there is no need to swab an inlet port with time sensitive medications already delivered to a patient. In some embodiments, there is not sufficient time to swab a connector between switching each of eight medications.

Further with multiple syringes attached to device, as in device 100 illustrated in FIG. 6, movement of the device can cause the connector at outlet 102 to come loose unless a spinning connector such as spinning luer lock connector 400 described herein is used. Further, a user may desire to turn the assembled device over which would otherwise cause the connector at outlet 102 to come loose. However, with the spinning connectors described herein, the assembled device can be turned over as desired without disconnection.

The devices described herein can be sterilized using any common sterilization technique without substantially degrading the device. In one embodiment, the sterilization method can be autoclaving, gamma radiation, or ethylene oxide. The devices can be sterilized before or after packaging.

In one embodiment, devices as described herein can be provided as kits for use. Any kit can include an appropriate packaging and instructions for use. Other information can be provided with the kits such as device dimensions, filter specifics, regulatory clearances/approvals, company information, marketing materials, and the like.

In some embodiments, a kit can include a device such as device 100 in an appropriate packaging with at least instructions for use.

In other embodiments, a kit can include a device such as device 100 in an appropriate packaging with a number of syringes that matches the number of inlets allowing only one syringe use per inlet. The kit can also include at least instructions for use.

In another embodiment, a kit can include a device such as device 100 in an appropriate packaging with colored inlet lines that represent what lines go to what filters. The kit can also include at least instructions for use.

In another embodiment, a kit can include a device such as device 100 in an appropriate packaging with colored inlet lines. A number of syringes color coded with the inlet lines can also be included. The kit can also include at least instructions for use.

In another embodiment, a kit can include a device such as device 100 including pre-filled syringes with medications directly from the pharmacy already attached to the device using a locked connector that cannot be removed from the device. The kit can also include at least instructions for use.

In another embodiment, a kit can include a device such as device 100 with colored inlet lines. A number of syringes color coded with the inlet lines can also be included that have been pre-filled by the pharmacy. The kit can also include at least instructions for use.

Methods of using the devices described herein to deliver multiple medications are also described. In one embodiment, a device as described herein, for example device 100 or device 600 can be unpackaged and its outlet port hooked into a patient's IV line using a luer style connector. Other connectors can also be used. Then, a first inlet port is aseptically prepared and/or scrubbed with an appropriate disinfectant for at least 15 seconds and a sterile medication syringe is attached to the scrubbed port. This process is repeated until all ports have been sterilized and syringes attached. Then, a provider delivers combinations of medications as needed by a patient.

This method allows all the medications or at least a majority of the medication syringes to be attached to the device and hence the IV line without the need to scrub a port to attach a separate syringe when a time sensitive medication has already been administered to a patient.

In another embodiment, a device as described herein, for example device 100 or device 600 can be unpackaged. Then, a first inlet port is aseptically prepared and/or scrubbed with an appropriate disinfectant for at least 15 seconds and a sterile medication syringe is attached to the scrubbed port. This process is repeated until all ports have been sterilized and syringes attached. The device's outlet port is then hooked into a patient's IV line. Then, a physician, advanced practice nurse, nurse, and/or provider can deliver combinations of medications as needed by a patient.

In other embodiments, a device as described herein, for example device 100 or device 600 can be unpackaged and its outlet port hooked into a patient's IV line. Then, a first inlet port with a particular color is aseptically prepared and/or scrubbed with an appropriate disinfectant for at least 15 seconds and a sterile medication syringe having a matching color is attached to the scrubbed port. This process is repeated until all ports have been sterilized and syringes attached. Then, a physician, advanced practice nurse, nurse, and/or provider delivers combinations of medications as needed by a patient.

In still another embodiment, a device as described herein, for example device 100 or device 600 can be unpackaged. Then, a first specifically colored inlet port is aseptically prepared and/or scrubbed with an appropriate disinfectant for at least 15 seconds and a sterile medication syringe of the matching color is attached to the scrubbed port. This process is repeated using matching syringes and ports until all ports have been sterilized and syringes attached. The device's outlet port is then hooked into a patient's IV line. Then, a physician, advanced practice nurse, nurse, and/or provider can deliver combinations of medications as needed by a patient.

The devices described herein can also interface with automated instruments. The devices can interface between an automated instrument and a patient's IV line. For example, device inlets can be connected to automated instrument outlets after appropriate port swabbing and the outlet of the device can be connected to the patient's IV line again after appropriate swabbing. The instrument can then deliver varying amounts of medications through the device and into the patient's IV line.

The devices described herein can also be included within an automated instrument and output contents to a patient's IV line. For example, device inlets can be connected within an automated instrument and the outlet of the device can be connected to the patient's IV line again after appropriate swabbing when the automated instrument is brought to a patient. The instrument can then deliver varying amounts of medications through the device and into the patient's IV line.

In some embodiments, two or more devices can be coupled together to add additional ports to a system. For example, a device with two inlets can have an inlet coupled to an outlet port of another device with two inlets. Subsequently, any number of additional devices can be added and chained together as appropriate. In one embodiment, there could be multiple automated instrument that deliver from large volume reservoir bags to small volume syringes via micro and/or macro tubing that all attach to one or a combination of devices that allow for one connection to the patient.

Example 1

Anesthesia Delivery

Prior to surgery in the operating room, a desired IV inlet port is aseptically prepared and/or scrubbed for at least 15 seconds to thoroughly disinfect the port. Then, a device as described herein is removed from its sterile packaging and attached to the IV inlet port. A patient who is prepped for joint replacement then enters the operating room.

Then, a first inlet port is aseptically prepared and/or scrubbed with an appropriate disinfectant for at least 15 seconds and a sterile medication syringe including an anesthesia such as propofol is attached to the first scrubbed port.

A second inlet port is then aseptically prepared and/or scrubbed with an appropriate disinfectant for at least 15 seconds and a sterile medication syringe including an antibiotic such as cefazolin is attached to the second scrubbed port.

A third inlet port is then aseptically prepared and/or scrubbed with an appropriate disinfectant for at least 15 seconds and a sterile medication syringe including a local anesthesia such as lidocaine is attached to the third scrubbed port.

A fourth inlet port is then aseptically prepared and/or scrubbed with an appropriate disinfectant for at least 15 seconds and a sterile medication syringe including a neuromuscular blocking agent such as rocuronium is attached to the fourth scrubbed port.

A fifth inlet port is then aseptically prepared and/or scrubbed with an appropriate disinfectant for at least 15 seconds and a sterile medication syringe including an anxiolytic/amnesic such as midazolam is attached to the fifth scrubbed port.

A sixth inlet port is then aseptically prepared and/or scrubbed with an appropriate disinfectant for at least 15 seconds and a sterile medication syringe including a narcotic such as fentanyl is attached to the sixth scrubbed port.

A seventh inlet port is then aseptically prepared and/or scrubbed with an appropriate disinfectant for at least 15 seconds and a sterile medication syringe including back up supply of anesthetic such as propofol attached to the seventh scrubbed port.

An eighth inlet port is then aseptically prepared and/or scrubbed with an appropriate disinfectant for at least 15 seconds and a sterile medication syringe including a blood pressure support medication such as ephedrine is attached to the eighth scrubbed port.

The eighth port can instead be loaded with an anti-nausea medication such as zofran. Alternatively, a device with nine inlet ports can be provided.

Further, the provider can turn the device including all syringes over without risking loosening of the outlet port to the IV inlet because of the rotating connector on the device.

Then, a provider delivers combinations of medications as needed by a patient without the need to remove and replace medications and waste time aseptically preparing and/or scrubbing ports once anesthesia has been initialized and anesthetizes the patient for surgery with a minimized risk of infection or patient risk.

Example 2

Anesthesia Delivery

A patient is rushed for a crash caesarean section under general anesthesia. The provider places an order to the pharmacy for a cocktail of medications to anesthetize the patient for surgery. A device as described herein with four syringes already connected is delivered to the operating room prior to the patient's arrival to the operating room. The preassembled device is delivered as follows: a first inlet port includes a sterile medication syringe including an anesthesia such as propofol; a second inlet port includes a sterile medication syringe including an antibiotic such as cefazolin; a third inlet port includes a sterile medication syringe including a narcotic such as fentanyl; a fourth inlet port includes a sterile medication syringe including a neuromuscular blocking agent such as succinylcholine.

The desired IV inlet port is aseptically prepared and/or scrubbed for at least 15 seconds to thoroughly disinfect the port. Then, the device is attached to the disinfected IV inlet port. The provider can turn the device including all syringes over without risking loosening of the outlet port to the IV inlet because of the rotating connector on the device.

Then, a provider delivers combinations of medications as needed by a patient without the need to remove and replace medications and waste time aseptically preparing and/or scrubbing ports once anesthesia has been initialized and anesthetizes the patient for surgery with a minimized risk of infection or patient risk.

Procedure related sedation which can occur in multiple hospital settings both in the emergency department, intensive care, and/or locations where anesthesia is administered for patients who require deep sedation only for the length of a procedure. Medications such as propofol can be combined with ketamine, etomidate, dexmeditomidine, fentanyl, midazalam, lidocaine or saline. Providing brief, titratable, deep sedation can be delivered by programmable automated instruments or directly by the provider.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A device for delivering at least two different medications, the device comprising:
    a body section including:
        a first inlet port including an anti-reflux valve and operably connected to a first smaller pore filter;
        a second inlet port including an anti-reflux valve and operably connected to a second larger pore filter;
        at least one additional inlet port connected to the first filter; and
        a rotating outlet port including a collar which surrounds the outlet port,
        wherein the collar includes a ratcheting mechanism having
            a gear including teeth and spaces between the teeth, wherein the gear runs around an internal circumference of the collar, and
            a delivery protrusion with pawls being lock into the spaces between the teeth, and wherein the pawls are only rotatable within the spaces between teeth;
    wherein the rotating outlet port is joined to the first filter and the second filter by a y-connector;
    wherein the rotating outlet port is configured to connect to an intravenous line such that the intravenous line is only allowed to disengage from the rotating outlet port by holding the collar when disconnecting the intravenous line; and
    wherein the device can be torqued while delivering the at least two different medications without loosening the rotating outlet port from the intravenous line.

2. The device of claim 1, wherein the first filter is a 0.2 μm filter.

3. The device of claim 2, wherein six inlet ports flow into the first filter.

4. The device of claim 1, wherein the second filter is a 5 μm filter.

5. The device of claim 2, wherein two inlet ports flow into the second filter.

6. The device of claim 1 including two inlet ports.

7. The device of claim 1, wherein the at least two inlet ports are scrubbable inlet ports.

8. The device of claim 1 including a minimal amount of dead space.

9. The device of claim 1, wherein the rotating outlet port is a male luer.

* * * * *